(12) United States Patent
Parce et al.

(10) Patent No.: US 7,150,814 B1
(45) Date of Patent: Dec. 19, 2006

(54) PREVENTION OF SURFACE ADSORPTION IN MICROCHANNELS BY APPLICATION OF ELECTRIC CURRENT DURING PRESSURE-INDUCED FLOW

(75) Inventors: J. Wallace Parce, Palo Alto, CA (US); Andrea W. Chow, Los Altos, CA (US)

(73) Assignee: Callper Life Sciences, Inc., Mountain View, CA (US)

( * ) Notice: Subject to any disclaimer, the term of this patent is extended or adjusted under 35 U.S.C. 154(b) by 481 days.

(21) Appl. No.: 10/214,961

(22) Filed: Aug. 8, 2002

Related U.S. Application Data (62) Division of application No. 09/310,027, filed on May 11, 1999, now Pat. No. 6,458,259.

(51) Int. Cl.
*G01N 27/453* (2006.01)
*G01N 30/02* (2006.01)

(52) U.S. Cl. .................... 204/600; 204/601; 422/70

(58) Field of Classification Search ........ 204/451–455, 204/601–605, 547, 643; 210/656; 422/70, 422/99, 100
See application file for complete search history.

(56) References Cited

U.S. PATENT DOCUMENTS

| | | | |
|---|---|---|---|
| 5,133,844 A | 7/1992 | Stevens | |
| 5,482,608 A * | 1/1996 | Keely et al. | 204/452 |
| 5,699,157 A | 12/1997 | Parce | |
| 5,779,868 A | 7/1998 | Parce et al. | |
| 5,800,690 A | 9/1998 | Chow et al. | |
| 5,842,787 A | 12/1998 | Kopf-Sill et al. | |
| 5,846,396 A * | 12/1998 | Zanzucchi et al. | 204/601 |
| 5,852,495 A | 12/1998 | Parce | |
| 5,869,004 A | 2/1999 | Parce | |
| 5,876,675 A | 3/1999 | Kennedy | |
| 5,880,071 A | 3/1999 | Parce et al. | |
| 5,882,465 A | 3/1999 | McReynolds | |
| 5,885,470 A | 3/1999 | Parce et al. | |
| 5,993,630 A | 11/1999 | Becker et al. | |
| 6,136,171 A | 10/2000 | Frazier et al. | |
| 6,221,654 B1 * | 4/2001 | Quake et al. | 435/287.3 |

FOREIGN PATENT DOCUMENTS

| | | |
|---|---|---|
| WO | WO 91/11262 A1 * | 8/1991 |
| WO | WO 93/16383 A1 * | 8/1993 |
| WO | WO 97/34689 A1 * | 9/1997 |
| WO | WO 98/00231 | 1/1998 |
| WO | WO 98/00705 | 1/1998 |
| WO | WO 98/00707 | 1/1998 |
| WO | WO 98-02728 | 1/1998 |
| WO | WO 98/05424 | 2/1998 |
| WO | WO 98/22811 | 5/1998 |
| WO | WO 98/45481 | 10/1998 |
| WO | WO 98/45929 | 10/1998 |
| WO | WO 98/46438 | 10/1998 |
| WO | WO 98/49548 | 11/1998 |
| WO | WO 98/55852 | 12/1998 |
| WO | WO 98/56956 | 12/1998 |
| WO | WO 99/00649 | 1/1999 |
| WO | WO 99/10735 | 3/1999 |

(Continued)

*Primary Examiner*—Alex Noguerola
(74) *Attorney, Agent, or Firm*—Donald R. McKenna; Ann C. Petersen (57) ABSTRACT

Methods and apparatus for reducing adsorption in microscale devices are provided. In the methods and apparatus, an electrical current such as an alternating current is applied to materials under pressure-induced flow. Integrated systems for simultaneous control of current and pressure in a channel are also provided.

24 Claims, 2 Drawing Sheets

Sample Flow Chart for Reduction of Surface Adhesion in an Integrated System

FOREIGN PATENT DOCUMENTS

| | | |
|---|---|---|
| WO | WO 99/12016 | 3/1999 |
| WO | WO 99/16162 | 4/1999 |
| WO | WO 99/19056 | 4/1999 |
| WO | WO 99/19516 | 4/1999 |
| WO | WO 99/29497 | 6/1999 |

* cited by examiner

PREVENTION OF SURFACE ADSORPTION IN MICROCHANNELS BY APPLICATION OF ELECTRIC CURRENT DURING PRESSURE-INDUCED FLOW

CROSS-REFERENCE TO RELATED APPLICATION

This application is a divisional of and claims the benefit of U.S. patent application Ser. No. 09/310,027 filed May 11, 1999, now U.S. Pat. No. 6,458,259, the disclosure of which is incorporated by reference.

BACKGROUND OF THE INVENTION

Surface adsorption of biological materials, such as proteins, to the walls of microscale fluid conduits can cause a variety of problems. For example, in assays relying on flow of material in the conduits, adsorption of test or reagent materials to the walls of the conduits (or to reaction chambers or other microfluidic elements) can cause generally undesirable biasing of assay results.

For example, charged biopolymer compounds can be adsorbed onto the walls of the conduits, creating artifacts such as peak tailing, loss of separation efficiency, poor analyte recovery, poor retention time reproducibility and a variety of other assay biasing phenomena. The adsorption is due, in part, e.g., to electrostatic interactions between, e.g., positively charged residues on the biopolymer and negatively charged groups resident on the surface of the separation device.

Reduction of surface adsorption in microscale applications is typically achieved by coating the surfaces of the relevant microscale element with a material which inhibits adsorption of assay components. For example, glass and other silica-based capillaries utilized in capillary electrophoresis have been modified with a range of coatings intended to prevent the adsorption of charged analytes to the walls of the capillaries. See, for example Huang et al., J. Microcol. Sep. 4, 135–143 (1992); Bruin et al., Journal of Chromatogr., 471, 429–436 (1989); Towns et al., Journal of Chromatogr., 599, 227–237 (1992); Erim, et al., Journal of Chromatogr., 708, 356–361 (1995); Hjerten, J. Chromatogr., 347, 191 (1985); Jorgenson, Trends Anal. Chem. 3, 51 (1984); and McCormick, Anal. Chem., 60, 2322 (1998). These references describe the use of a variety of coatings, including surface derivatization with poly(ethyleneglycol) and poly(ethyleneimine), functionalization of poly(ethyleneglycol)-like epoxy polymers as surface coatings, functionalization with poly(ethyleneimine) and coating with polyacrylamide, polysiloxanes, glyceroglycidoxypropyl coatings and others. Surface coatings have also been used for, e.g., modification of electroosmotic potential of the relevant microscale surface e.g., as taught in U.S. Pat. No. 5,885,470, CONTROLLED FLUID TRANSPORT IN MICROFABRICATED POLYMERIC SUBSTRATES by Parce et al.

Other than the use of surface coatings, few approaches exist for controlling surface adsorption of biopolymers in microscale systems. In general, other design parameters used to control adsorption include the material used in the device, modulation of flow rates and the like. Generally, surface adsorption of biological materials in capillary fluidics applications is a significant issue for at least some applications, and additional mechanisms for inhibiting surface adsorption in microfluidic applications are desirable. The present invention provides new strategies for inhibiting surface adsorption of polymers, molecules and biological materials, e.g., in pressure-based microscale flow applications. Additional features will become apparent upon complete review of the following disclosure.

SUMMARY OF THE INVENTION

The present invention derives from the surprising discovery that electroosmotic flow can be used in a pressure-driven microfluidic system to modulate surface adsorption. In particular, application of an electric field in a fluidic conduit during pressure-based flow prevents or reduces adsorption of materials such as proteins from adhering to the walls of a microchannel or other microscale element. Thus, application of an electric field during pressure-based flow can be used to reduce adsorption of proteins and other molecules or materials to the walls of the microscale element. Thus, application of electrokinetic force during pressure based flow can be regular and reversible, e.g., as applied by an alternating current. In this embodiment, movement of components in a microscale conduit due to electrokinetic forces can be minimized, a desirable feature, e.g., for applications in which separation of materials by charge is not desired.

Accordingly, the invention provides methods of regulating surface adsorption in a channel. In the method, a fluid is flowed through a channel by applying pressure to the fluid in the channel. An electric field (which is alternating or constant) is continuously or periodically applied to the fluid in the channel. The electric current field can be used as an additional motive force directing movement of a material in the fluid (or directing the fluid itself, as occurs, e.g., during electroosmosis) adding or subtracting from the pressure-based velocity of the material in the channel (electrokinetic and pressure-based flow effects can have the same or an opposite force vector). Alternatively, the electric field can be applied in such a way that the effects of the electric field on the overall velocity of the material are negligible or non-existent (e.g., other than at the walls of the conduit, where the electric field modulates adsorption). For example, the overall contribution to the velocity of a fluid or material in a fluid, exclusive of adsorption effects can be anywhere from 0.1× of the total velocity or less, to less than 50% of the total velocity (0.5×) to 90% of the total velocity (0.9×) or more. For example when using alternating current, there may be essentially no contribution to velocity of fluids or materials in the fluids.

A variety of fields and current types can be used in the methods of the invention. For example, an alternating square wave or sine wave field can be applied. Similarly, adsorption of a variety of materials can be regulated by the application of electric fields, including proteins, cells, carbohydrates, nucleic acids, lipids and a combination thereof. Application of the electric field can be simultaneous with application of a pressure gradient, or pressure and electrokinetic forces can be alternated. Pressure gradients can be applied by any of a variety of methods, including use of a vacuum source, a hydraulic pressure source, a pneumatic pressure source, an electroosmotic pressure pump, or contact with an absorbent material or a set of fluidly coupled capillary channels.

The use of electrokinetic movement of materials during pressure-induced flow can also be used in conjunction with other methods of eliminating surface adsorption. For example, a coating can be applied to a microscale element to additionally reduce adsorption, or, e.g., to provide for electroosmosis.

In addition to the use of electrical current to prevent adsorption of materials to walls of conduits, adsorption prevention agents can also be used to reduce unwanted adsorption, including, e.g., detergents and blocking agents (e.g., a combination of NDSB and BSA). These adsorption prevention agents can be used in place of or in concert with application of electric fields for reduction of surface adsorption.

Devices and systems for practicing the methods of the invention are also provided. The devices and systems include a body having a one or a plurality of fluidly coupled microchannels disposed therein. A source of fluidic material is fluidly coupled to at least one of the plurality of microchannels. A fluid pressure controller is fluidly coupled to the at least one microchannel and at least two electrodes are in fluidic or ionic contact with the at least one microchannel. An electrical controller is typically in electrical contact with the at least two electrodes. In a preferred embodiment, the electrical controller applies an alternating electrical field between the at least two electrodes. Typically, the device is configured to apply an electric field of sufficient duration and intensity to dislodge a protein from a surface of the at least one microchannel, or to prevent protein binding to a surface of the at least one microchannel.

In general, the device or system can be configured for electrokinetic or pressure-based flow, or both. For example, flow can be primarily driven by pressure with a small or negligible contribution by electrokinetic forces, or, optionally, the electrokinetic forces can contribute similar or even greater velocity to a material or fluid than the pressure-based forces. In one aspect, the electrical controller is configured to minimize movement of the fluidic material in a direction of fluid flow, or to minimize movement of charged fluidic material in the direction of flow of the charged material. Typically, the fluid pressure controller and the electrical controller concomitantly apply a fluid pressure gradient and an electric field in the at least one channel. Thus, the device or system can include a control element such as a computer with an instruction set for simultaneously regulating electrical current and fluidic pressure in the at least one channel (or any other microscale element in the device). For example, the computer can regulate electrical current, e.g., to control adsorption of biological materials in conduits in the microscale system.

The body of the device or system is typically fabricated from one or more material(s) commonly used in microscale fabrication, including ceramics, glass, silicas, and plastics or other polymer materials. The microscale elements (e.g., microchannels) within the body structure typically have at least one dimension between about 0.1 and 500 microns. Ordinarily, the body has a plurality of intersecting microchannels formed into a channel network.

As noted, the device or system will ordinarily include an alternating current electrical controller e.g., which is capable of generating a sine or square wave field, or other oscillating field.

The device or system will ordinarily include a signal detector mounted proximal to a signal detection region, fluidly coupled to the at least one microchannel. This detector can be configured to monitor any detectable event, e.g., an optical, thermal, potentiometric, radioactive or pH-based signal.

In one aspect, the invention includes an integrated system for moving adherent materials in a microchannel. The integrated system includes a first microchannel fluidly coupled to a pressure source and to a plurality of electrodes. A fluid pressure modulator modulates pressure at the pressure source. An electrical controller modulates current or voltage at least at two of the plurality of electrodes. A computer is operably linked to the fluid pressure modulator and to the electrical controller. The computer has an instruction set for controlling the fluid pressure modulator and the electrical controller. This instruction set provides for reduced adsorption of the adherent materials to a surface of the microchannel during pressure-induced flow of the materials. As noted, the integrated system can include a signal detector proximal to a signal detection zone that is fluidly coupled to the microchannel. The integrated system optionally includes a body structure having the first microchannel disposed therein. The integrated system can include a plurality of additional microchannels disposed in the body structure which are fluidly coupled to the first microchannel. The additional microchannels are fluidly coupled to a source of one or more fluidic reagents, with the computer optionally including an instruction set which directs movement of at least one of the one or more fluidic reagents into the first microchannel.

Similarly, the integrated system can include a flow sensor, which senses the rate of flow of one or more fluidic component in the microchannel. In this embodiment, the computer has an instruction set directing the electrical controller to apply an electric field in response to the rate of flow of the one or more fluidic component.

Definitions

Unless specifically indicated to the contrary, the following definitions supplement those in the art for the terms below.

"Microfluidic," as used herein, refers to a system or device having fluidic conduits or chambers that are generally fabricated at the micron to submicron scale, e.g., typically having at least one cross-sectional dimension in the range of from about 0.1 μm to about 500 μm. The microfluidic systems of the invention are fabricated from materials that are compatible with the conditions present in the particular experiment of interest. Such conditions include, but are not limited to, pH, temperature, ionic concentration, pressure, and application of electrical fields. The materials of the device are also chosen for their inertness to components of the experiment to be carried out in the device. Such materials include, but are not limited to, glass and other ceramics, quartz, silicon, and polymeric substrates, e.g., plastics, depending on the intended application.

A "microscale cavity" is a conduit or chamber having at least one dimension between about 0.1 and 500 microns.

A "microchannel" is a channel having at least one microscale dimension, as noted above. A microchannel optionally connects one or more additional structure for moving or containing fluidic or semi-fluidic (e.g., gel- or polymer solution-entrapped) components.

A "microwell plate" is a substrate comprising a plurality of regions which retain one or more fluidic components.

A "pipettor channel" is a channel in which components can be moved from a source to a microscale element such as a second channel or reservoir. The source can be internal or external (or both) to the main body of a microfluidic device comprising the pipettor channel.

An "electric current" is a flow of charge from one place to another. The typical unit of current flow is the ampere. For purposes of this disclosure, an "electric field" exists wherever an electric or ionic force acts on a charged element (particle, atom, molecule, etc.). In the context of a microscale channel, an electric field of the invention can be, e.g., an electronic or ionic gradient across a selected microchannel region or area. Thus, typically, electrodes are positioned in wells which are fluidly coupled to channel termini. In this configuration, the electrodes are in electrical contact with fluid in the wells (i.e., where electrons travel to or from the fluid into or from the electrode) and in ionic contact with fluid in the channels.

A "direct current" is typically described in terms of its direction and magnitude. The current flows in a specified direction, with a specified magnitude of flow (e.g., a current between a positive electrode and a negative electrode could be, e.g., 1 milliamp). Classically, the direction of an electric field is the direction of the force on a positive test charge (real or hypothetical) placed at a specified point in the electric field (the force on a negative charge such as an electron is, therefore, opposite the "direction" of the field). In an "alternating current," the current flows back and forth between two or more specified points in a circuit, e.g., in a microfluidic system, two electrodes connected by an fluid comprising ionizable elements. This back and forth flow is typically, though not necessarily, regular. Thus, alternating current (AC) has a frequency (e.g., the number of times the flow goes through a complete cycle per unit time) and an amplitude. The function used to describe the profile of the AC can be essentially any regular repeating wave form. Common wave forms include trigonometric functions (e.g., sine or cosine waves), square waves and an essentially infinite variety of other functions. One of the most common AC forms is sine wave AC, with the variation of the alternating current with time following the formula $I=I_{max}\sin 2\pi ft$ where I is the current, $I_{max}$ is the maximum current, f is the frequency of the current and t is the specified time (typically, I=0 and is increasing, when t=0). By analogy with circular motion, angular frequency ω (in radians per second) is often used in discussions of sinusoidal alternating currents instead of frequency f (e.g. in hertz), where $\omega=2\pi f$ and the instantaneous current in an ac circuit is $I=I_{max}\sin \omega t$. For a typical sine wave alternating current, the effective current ($I_{eff}$) is $$I_{eff} = \frac{I_{max}}{\sqrt{2}}.$$

Similarly, for a typical sinusoidal ac, the effective voltage ($V_{eff}$) is $$V_{eff} = \frac{V_{max}}{\sqrt{2}}.$$

Both AC and DC can exist as wave functions, e.g., as described above for AC, and where the current is varied between 0 and a selected $I_{max}$. For example, a "square wave" can be either DC or AC, or have both DC and AC components. A square wave is characterized by an abrupt wave function in which the transition between $I_{max}$ and $I_{min}$ is very rapid (for a perfect square wave, the transition is instantaneous). Both AC and DC functions can be present simultaneously. For example, an AC/DC square wave exists where direct current is turned off and on repeatedly and abruptly. An AC square wave exists where the current oscillates between $I_{max}$ and $I_{min}$ with a fast or even essentially instantaneous transition between the two. It should be noted that, for purposes of this disclosure, a "square wave" includes closely related wave forms, i.e., where the transition between $I_{max}$ and $I_{min}$ is substantially more abrupt than the transition that occurs for a sine wave current (i.e., where the transition between $I_{max}$ and $I_{min}$ is more rapid than for a sine wave current), even if the transition is not actually instantaneous.

Pressure or electrokinetic forces "significantly" direct flow of a specified material when the force contributes at least 25% of the total forward velocity of the material, or where the force inhibits flow by at least 25% in the direction of flow (e.g., where electrokinetic and pressure based forces have an opposite force vector, e.g., where the pressure and electrokinetic effects are "counter current").

BRIEF DESCRIPTION OF THE DRAWING

FIG. 2, panels A and B are schematic diagrams of pressure and electroosmotic flow configurations.

DETAILED DISCUSSION OF THE INVENTION

The invention relates to the reduction and prevention of surface adsorption of materials to microchannel walls and other microscale elements in microfluidic systems. It was determined that binding to the surface of microscale elements was problematic in flowing assays and material separations for proteins, cells, carbohydrates, nucleic acids, lipids and other materials during pressure-based flow of the materials. This was due, in part, to the fact that the rate of flow (flow velocity) of materials at the walls in a microscale channel typically is lower than the rate of flow of the materials in the interior of the microscale channel. This low flow rate increases the time that a material remains in position proximal to a given region of the microscale channel. This increased proximity to a single region leads to formation of strong interactions between the channel region and the material.

In contrast, in electroosmotic flow systems, maximal material velocity is ordinarily achieved at the walls of the microscale channels, typically at about 10–15 Å from the surface of the wall. The diameter of many biological materials is large with respect to this distance. For purposes of this disclosure, the diameter of a material is "large" with respect to this distance when the average diameter of the material is at least about 5 Å, typically at least about 10 Å, often at least about 20 Å, generally at least about 50 Å or more in diameter. For example, the diameter of the protein hemoglobin is about 55 Å, and is "large" with respect to a measurement of 10–15 Å. Large biological molecules such as cells are, of course, large as compared to the region of maximal flow velocity.

Data suggested that the kinetics of surface adsorption during flow for many materials includes several steps. First, a low affinity association occurs between the material and a wall of a conduit through which the material is being flowed. This low affinity association is relatively short in duration and is followed by a higher affinity interaction that is relatively longer lived. This higher affinity interaction can give way to an even higher affinity interaction in which the material becomes essentially permanently adhered to the surface. In this state, the material can exist in a denatured, or at least in a non-solution phase state. Once the material achieves the high affinity interaction, it is difficult to displace from the wall of the conduit.

Because of the flow profile during pressure-based flow, the velocity of many biological and other materials is close to 0 at the wall of a microscale conduit during pressure-based flow. This low flow velocity provides time for high affinity binding between the material and the wall of the conduit to occur. In contrast, because the flow velocity during electroosmotic flow is highest at the walls of the conduit through which electroosmotic flow takes place, materials do not have time to form high affinity interactions with the walls of the conduit. Thus, applying an electric field during pressure-based flow reduces unwanted adsorption of materials to the conduit walls. The use of alternating fields (e.g., square or sine AC waves) eliminates electroosmotic material movement (i.e., in applications where electroosmosis is not desirable) while still keeping materials at the walls of the conduit in motion and preventing unwanted surface adsorption of the materials to the walls.

Typically, current is applied to microscale systems for a time (ts) sufficient to prevent surface adsorption of a material, or to reduce adsorption. ts varies for different materials, but, in general, is of sufficient duration to modulate velocity of fluid, ions or materials at the walls of a channel or other microscale structure. This can be determined empirically for a given material and fluid, e.g., using the techniques discussed for monitoring adsorption noted below.

In addition to the use of electrical current to reduce surface adsorption, the present invention provides for the use of adsorption prevention agents such as detergents (NDSB, Triton x-100, SDS, etc.) and blocking agents (e.g., BSA and reconstituted non-fat dry milk) to reduce surface adsorption of materials of interest. These adsorption prevention agents can be used in concert with, or separate from the use of electric currents to prevent adsorption of materials to microscale structures. Typically, the concentration of detergent is about 0.05 M to 1 M (typically about 0.1 M) and the concentration of blocking protein is about 0.05 mg/ml to 1 mg/ml, typically about 0.1 mg/ml.

Flow of Materials in Microscale Devices

Materials are typically flowed in microscale systems by application of electrokinetic forces or by the application of fluid pressure. In addition, electrokinetic forces can be used to induce fluidic pressure at sites upstream or downstream of the application of the electrokinetic force.

Pressure-Based Flow in Microscale Systems

Pressure forces can be applied to microscale elements to achieve fluid movement using any of a variety of techniques. Fluid flow (and flow of materials suspended or solubilized within the fluid) is optionally regulated by pressure based mechanisms such as those based upon fluid displacement, e.g., using a piston, pressure diaphragm, vacuum pump, probe or the like to displace liquid and raise or lower the pressure at a site in the microfluidic system. The pressure is optionally pneumatic, e.g., a pressurized gas, or uses hydraulic forces, e.g., pressurized liquid, or alternatively, uses a positive displacement mechanism, i.e., a plunger fitted into a material reservoir, for forcing material through a channel or other conduit.

In other embodiments, a vacuum source is applied to a reservoir or well at one end of a channel to draw the suspension through the channel. Pressure or vacuum sources are optionally supplied external to the device or system, e.g., external vacuum or pressure pumps sealably fitted to the inlet or outlet of the channel, or they are internal to the device, e.g., microfabricated pumps integrated into the device and operably linked to the channel. Examples of microfabricated pumps have been widely described in the art. See, e.g., published International Application No. WO 97/02357.

Hydrostatic, wicking and capillary forces can also be used to provide pressure for fluid flow. See, e.g., "METHOD AND APPARATUS FOR CONTINUOUS LIQUID FLOW IN MICROSCALE CHANNELS USING PRESSURE INJECTION, WICKING AND ELECTROKINETIC INJECTION," by Alajoki et al., U.S. Ser. No. 09/245,627, filed Feb. 5, 1999. In these methods, an adsorbent material or branched capillary structure is placed in fluidic contact with a region where pressure is applied, thereby causing fluid to move towards the adsorbent material or branched capillary structure.

In an alternate embodiment, microfluidic systems can be incorporated into centrifuge rotor devices, which are spun in a centrifuge. Fluids and particles travel through the device due to gravitational and centripetal/centrifugal pressure forces.

Fluid flow can, of course, also be due to electrokinetic forces as noted below. In a preferred aspect, fluid downstream or upstream of a region in which pressure-based flow is desired is subjected to electrokinetic force. The electrokinetic movement of fluid in these regions causes a pressure wave in fluidly coupled regions such as the region where pressure-based flow is desired, thereby causing fluid movement. Such "electroosmotic pressure pumps" are desirable where, e.g., fine control of fluid forces is desired.

Electrokinetic Flow

One method of achieving transport or movement of materials through microfluidic channels is by electrokinetic material transport. "Electrokinetic material transport systems," as used herein, includes systems that transport and direct materials within a microchannel and/or chamber containing structure, through the application of electrical fields to the materials, thereby causing material movement through and among the channels and/or chambers, i.e., cations will move toward a negative electrode, while anions will move toward a positive electrode. For example, movement of fluids toward or away from a cathode or anode can cause movement of particles suspended within the fluid (or even particles over which the fluid flows).

In general, electrokinetic material transport and direction systems include those systems that rely upon the electrophoretic mobility of charged species within the electric field applied to the structure, or which rely upon electroosmotic flow of fluids.

A variety of electrokinetic controllers are described, e.g., in Ramsey WO 96/04547, Parce et al. WO 98/46438 and Dubrow et al., WO 98/49548, as well as a variety of other references by the inventors and their co-workers as noted herein.

To provide appropriate electric fields, the system generally includes a voltage controller that is capable of applying selectable voltage levels, simultaneously or sequentially, e.g., to a plurality of reservoirs fluidly coupled to microscale channels. Such a voltage controller is optionally implemented using multiple voltage dividers and multiple relays to obtain the selectable voltage levels. Alternatively, multiple independent voltage sources are used. The voltage controller is electrically connected to each of the reservoirs via an electrode positioned or fabricated within each of the plurality of reservoirs. In one embodiment, multiple electrodes are positioned to provide for irregular switching of the electric field direction in a microchannel, thereby causing the analytes to travel along a microchannel, with a longer distance than the physical length of the microchannel. Use of electrokinetic transport to control material movement in interconnected channel structures was described, e.g., in WO 96/04547 to Ramsey. An exemplary controller is described in U.S. Pat. No. 5,800,690. Modulating voltages are concomitantly applied to the various reservoirs to affect a desired fluid flow characteristic, e.g., continuous or discontinuous (e.g., a regularly pulsed field causing the sample to oscillate direction of travel) flow of labeled components toward a waste reservoir. Particularly, modulation of the voltages applied at the various reservoirs can move and direct fluid flow through the interconnected channel structure of the device.

As noted elsewhere, one preferred embodiment of the present invention includes application of an alternating current to eliminate adsorption of materials such as proteins to the walls of microfluidic conduits. Alternating power supplies are known and available and can be connected to electrodes to deliver alternating current to electrodes which are fluidly coupled to a microfluidic channel or other structure. As noted, this channel is typically coupled to a pressure control element (e.g., hydraulic, pneumatic, capillary or electroosmotic pump element). Thus, the devices and systems of the invention typically provide for simultaneous or sequential application of fluidic force and alternating current to one or more microchannels within the device.

In addition to reducing surface adsorption, AC can be used during pressure or EO based flow to achieve joule heating of materials in a channel or channel region, e.g., for performing thermocyclic reactions such as PCR during pressure or EO based flow. Alternating current used to heat fluids can be selectively adjusted to complement voltage or electric field that may be applied between selected regions which are used for fluid movement, e.g., concurrent with pressure-based fluid movement or for reducing/preventing surface adsorption.

In general, AC, voltage, and/or frequency can be adjusted, for example, to heat the fluid without substantially influencing movement of the fluid, or to provide minimal heating (e.g., for simply reducing adsorption), optionally without substantially altering fluid movement. In general, a power supply can apply any combination of DC, AC, and pulse current (a brief burst of current which may be AC or DC), depending upon the application.

Integrated Systems and Devices

The inventors and their co-workers have provided a variety of microfluidic systems which can be adapted to the present invention by including both pressure and electrokinetic control elements to the systems. For example, Ramsey WO 96/04547 provides a variety of microfluidic systems. See also, Ramsey et al. (1995), *Nature Med.* 1(10):1093–1096; Kopf-Sill et al. (1997) "Complexity and performance of on-chip biochemical assays," *SPIE* 2978: 172–179 February 10–11; Bousse et al. (1998) "Parallelism in integrated fluidic circuits," *SPIE* 3259:179–186; Chow et al. U.S. Pat. No. 5,800,690; Kopf-Sill et al. U.S. Pat. No. 5,842,787; Parce et al., U.S. Pat. No. 5,779,868; Parce, U.S. Pat. No. 5,699,157; Parce et al. WO 98/00231 Parce et al. WO 98/00705; Chow et al. WO 98/00707; Parce et al. WO 98/02728; Chow WO 98/05424; Parce WO 98/22811; Knapp et al., WO 98/45481; Nikiforov et al. WO 98/45929; Parce et al. WO 98/46438; Dubrow et al., WO 98/49548; Manz, U.S. Pat. No. 5,296,114 and e.g., EP 0 620 432 A1; Seiler et al. (1994) *Mitt Gebiete Lebensm. Hyg.* 85:59–68; Seiler et al. (1994) *Anal. Chem.* 66:3485–3491; Jacobson et al. (1994) "Effects of Injection Schemes and Column Geometry on the Performance of Microchip Electrophoresis Devices" Anal. Chem. 66: 66. 1107–1113; Jacobsen et al. (1994) "Open Channel Electrochromatograpy on a Microchip" *Anal. Chem.* 66:2369–2373; Jacobsen et al. (1994) "Precolumn Reactions with Electrophoretic Analysis Integrated on Microchip" *Anal. Chem.* 66:4127–4132; Jacobsen et al. (1994) "Effects of Injection Schemes and Column Geometry on the Performance of Microchip Electrophoresis Devices." *Anal. Chem.* 66:1107–1113; Jacobsen et al. (1994) "High Speed Separations on a Microchip." *Anal. Chem.* 66:1114–1118; Jacobsen and Ramsey (1995) "Microchip electrophoresis with sample stacking" Electrophoresis 16:481–486; Jacobsen et al. (1995) "Fused Quartz Substrates for Microchip Electrophoresis" *Anal. Chem.* 67: 2059–2063; Harrison et al. (1992) "Capillary Electrophoresis and Sample Injection Systems Integrated on a Planar Glass Chip." *Anal. Chem.* 64:1926–1932; Harrison et al. (1993) "Micromachining a Miniaturized Capillary Electrophoresis-Based Chemical Analysis System on a Chip." *Science* 261:895–897; Harrison and Glavania (1993) "Towards Miniaturized Electrophoresis and Chemical System Analysis Systems on Silicon: An Alternative to Chemical Sensors." *Sensors and Actuators* 10:107–116; Fan and Harrison (1994) "Micromachining of Capillary Electrophoresis Injectors and Separators on Glass Chips and Evaluation of Flow at Capillary Intersections". *Anal. Chem.* 66: 177 –184; Effenhauser et al. (1993) "Glass Chips for High-Speed Capillary Electrophoresis Separations with Submicrometer Plate Heights" *Anal. Chem.* 65:2637–2642; Effenhauser et al. (1994) "High-Speed Separation of Antisense Oligonucleotides on a Micromachined Capillary Electrophoresis Device." *Anal. Chem.* 66:2949–2953; and Kovacs EP 0376611 A2.

Complete integrated microfluidic systems of the invention can include pressure and/or electrokinetic fluid handling elements, signal detection elements, sample storage and sample accessing subunits, AC power supplies coupled to electrodes which are fluidly connected to microchannels or other microscale element, computers or microprocessors operably coupled to the AC power with instruction sets for reducing adsorption of materials in the microfluidic system, signal detection subunits, a source of one or more adsorption prevention agent fluidly coupled to the microchannel, etc.

Integrated systems of the prior art can be adapted to the present invention by providing elements for AC or other electrokinetically controlled processes for reducing surface adsorption, typically in concert with pressure-based fluid handling elements coupled to a given microchannel. For example, Parce et al. "High Throughput Screening Assay Systems in Microscale Fluidic Devices" WO 98/00231 and Knapp et al. "Closed Loop Biochemical Analyzers" (WO 98/45481; PCT/US98/06723) provide pioneering technology for the integration of microfluidics and sample selection and manipulation. For example, in WO 98/45481, microfluidic apparatus, methods and integrated systems are provided for performing a large number of iterative, successive, or parallel fluid manipulations.

Figure 1:
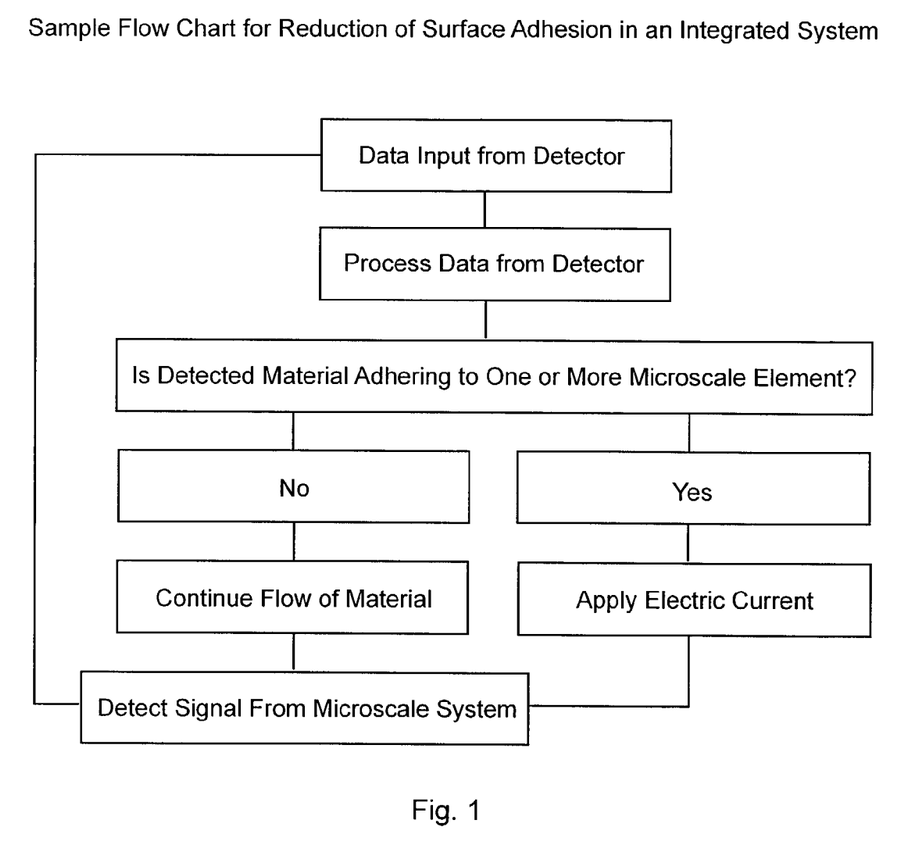
FIG. 1 is a schematic of an example flow chart of process steps performed in one embodiment of an integrated system of the invention.

In general, these systems are adapted to the present invention by providing electrokinetic control elements, e.g., for application of alternating current in a channel, e.g., during pressure-based flow of materials. Typically, the electrokinetic and fluid pressure control elements are operably linked to one or more computer comprising an instruction set for applying current such as AC for reduced adsorption of materials in the channels while simultaneously or sequentially applying a pressure differential to a channel. For example, these microfluidic systems can be adapted for use in the present invention, i.e., by using electric current to reduce adsorption during pressure-based flow of materials in the devices. FIG. 1 schematically represents one embodiment with feedback for determining whether to apply AC to reduce surface adsorption. In other embodiments, AC is applied regularly or intermittently without monitoring the effect of the current on adsorption. A variety of other approaches are also noted herein.

Detectors

The devices herein optionally include signal detectors, e.g., which detect fluorescence, phosphorescence, radioactivity, pH, charge, absorbance, luminescence, temperature, magnetism or the like. The detectors optionally monitor a plurality of signals from the plurality of materials, either simultaneously or sequentially. For example, the detector can monitor a plurality of optical signals which correspond in position to sets of materials within the device. Example detectors include photo multiplier tubes, CCD array elements, a scanning detector or galvo-scann or the like. Assay components which emit a detectable signal can be flowed past the detector, or, alternatively, the detector can move relative to the microscale elements of the device to determine component position (or, preferably, the detector can simultaneously monitor a number of spatial positions corresponding to assay members, e.g., as in a CCD array). The detector can include or be operably linked to a computer, e.g., which has software for converting detector signal information into nucleic acid sequence information, converting detector signal information into reaction kinetic information, converting signal information into antibody binding data, converting signal information into cell receptor binding data converting signal information into hybridization data, or the like.

Signals from devices are optionally calibrated, e.g., by calibrating the microfluidic system by monitoring a signal from a known material or other component. Similarly the relative positions of materials and signals from the devices are monitored, e.g., by determining the position of one or more materials by monitoring a signal from a known component, thereby determining the position of the known component.

In the microfluidic systems described herein, a variety of detection methods and systems are employed, depending upon the specific operation that is being performed by the system. A microfluidic system can also employ multiple different detection systems for monitoring the output of the system. Detection systems of the present invention are used to detect and monitor the materials in e.g., a detection window. Once detected, the flow rate and velocity of materials in the channels is optionally measured and controlled.

Examples of detection systems include optical sensors, temperature sensors, pressure sensors, pH sensors, conductivity sensors, and the like. Each of these types of sensors is readily incorporated into the microfluidic systems described herein. In these systems, such detectors are placed either within or adjacent to the microfluidic device or one or more channels, chambers or conduits of the device, such that the detector is within sensory communication with the device, channel, or chamber. The phrase "within sensory communication" of a particular region or element, as used herein, generally refers to the placement of the detector in a position such that the detector is capable of detecting the property of the microfluidic device, a portion of the microfluidic device, or the contents of a portion of the microfluidic device, for which that detector was intended. For example, a pH sensor placed in sensory communication with a microscale channel is capable of determining the pH of a fluid disposed in that channel. Similarly, a temperature sensor placed in sensory communication with the body of a microfluidic device is capable of determining the temperature of the device itself.

Detection systems optionally include optical detection systems for detecting an optical property of a material within the channels and/or chambers of the microfluidic devices that are incorporated into the microfluidic systems described herein. Such optical detection systems are typically placed adjacent to a microscale channel of a microfluidic device, and are in sensory communication with the channel via an optical detection window that is disposed across the channel or chamber of the device. Optical detection systems include systems that are capable of measuring the light emitted from material within the channel, the transmissivity or absorbance of the material, as well as the materials spectral characteristics. In preferred aspects, the detector measures an amount of light emitted from the material, such as a fluorescent or chemiluminescent material. As such, the detection system will typically include collection optics for gathering a light based signal transmitted through the detection window, and transmitting that signal to an appropriate light detector. Microscope objectives of varying power, field diameter, and focal length are readily utilized as at least a portion of this optical train. The light detectors are optionally photodiodes, avalanche photodiodes, photomultiplier tubes, diode arrays, or in some cases, imaging systems, such as charged coupled devices (CCDs) and the like. In preferred aspects, photodiodes are utilized, at least in part, as the light detectors. The detection system is typically coupled to a computer (described in greater detail below), via an analog to digital or digital to analog converter, for transmitting detected light data to the computer for analysis, storage and data manipulation.

In the case of fluorescent materials, the detector will typically include a light source which produces light at an appropriate wavelength for activating the fluorescent material, as well as optics for directing the light source through the detection window to the material contained in the channel or chamber. The light source can be any number of light sources that provides an appropriate wavelength, including lasers, laser diodes and LEDs. Other light sources required for other detection systems. For example, broad band light sources are typically used in light scattering/transmissivity detection schemes, and the like. Typically, light selection parameters are well known to those of skill in the art.

The detector can exist as a separate unit, but is preferably integrated, with the controller system, into a single instrument. Integration of these functions into a single unit facilitates connection of these instruments with the computer (described below), by permitting the use of few or a single communication port(s) for transmitting information between the controller, the detector and the computer.

Computer Interface

As noted above, either or both of the controller system and/or the detection system are coupled to an appropriately programmed processor or computer which functions to instruct the operation of these instruments in accordance with preprogrammed or user input instructions, receive data and information from these instruments, and interpret, manipulate and report this information to the user. As such, the computer is typically appropriately coupled to one or both of these instruments (e.g., including an analog to digital or digital to analog converter as needed).

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the fluid direction and transport controller and adsorption inhibition elements (e.g., AC power source) to carry out the desired operation. The computer then receives the data from the one or more sensors/detectors included within the system, and interprets the data, either providing it in a user understood format, or using that data to initiate further controller instructions, in accordance with the programming, e.g., such as in monitoring and/or controlling of flow rates, pressure gradients, temperatures, applied voltages, and the like.

In the present invention, the computer can include software for the monitoring of detector signals produced by material in the channels, so that flow rate and velocity may be determined and modulated. Additionally the software is optionally used to control electrokinetic or pressure-based injection or withdrawal of material. The injection or withdrawal is optionally used to modulate the flow rate as described above.

Kits

Generally, the microfluidic devices described herein are packaged to include many, if not all, of the reagents for performing the device's preferred function. For example, the kits can include any of microfluidic devices comprising an interface for connecting to an adsorption elimination agent (e.g., leads for coupling to an AC power source, or wells for receiving electrodes coupled to the AC power source) reagents (e.g., protein assay components, nucleic acid sequencing reagents, PCR reagents, etc.), sample materials, control materials, or the like. Such kits also typically include appropriate instructions for using the devices and reagents, and in cases where reagents are not predisposed in the devices themselves, with appropriate instructions for introducing the reagents into the channels and/or chambers of the device. In this latter case, these kits optionally include special ancillary devices for introducing materials into the microfluidic systems, e.g., appropriately configured syringes/pumps, or the like (of course, in one preferred embodiment, the device itself comprises a pipettor element, such as an electropipettor for introducing material into channels and chambers within the device). In the former case, such kits typically include a microfluidic device with necessary reagents predisposed in the channels/chambers of the device. Generally, such reagents are provided in a stabilized form, so as to prevent degradation or other loss during prolonged storage, e.g., from leakage. A number of stabilizing processes are widely used for reagents that are to be stored, such as the inclusion of chemical stabilizers (i.e., enzymatic inhibitors, microcides/bacteriostats, anticoagulants), the physical stabilization of the material, e.g., through immobilization on a solid support, entrapment in a matrix (i.e., a gel), lyophilization, or the like.

Example Flow Diagram

FIG. 1 is an example flow diagram outlining elements of an integrated system of the invention. In this embodiment, computer control is used to apply electric current when appropriate to reduce adhesion. In other embodiments, feedback control is not performed and, instead, current is simply applied continuously or regularly without monitoring adhesion.

Measuring Reduced Surface Adsorption

A variety of approaches are appropriate for monitoring surface adsorption of selected materials in microscale systems and any available method for measuring adsorption of materials to microscale system elements can be adapted to the present invention.

The precise methodology appropriate to monitoring reduced surface adsorption depends on the material at issue. Where materials can be viewed optically (e.g., using a microscope), such as where the materials are cells, adsorption can be directly monitored by simply viewing a portion of the channel through which the material is flowed. Adsorption is characterized by immobilization of the material in a region of the channel. Materials such as proteins and nucleic acids can be made viewable by incorporation of labels such as fluorophores, radioactive labels, labeled antibodies, dyes and the like, and can similarly be directly monitored by detecting label signal levels in a portion of the channel.

In addition to direct detection methods, indirect adsorption detection methods are also appropriate. For example, controls comprising assay elements for a control assay can be flowed through a channel and the results of the assay monitored and compared to expected results. Where the results of the assay are not as predicted (e.g., where enzyme concentration appears to increase constantly over time), or change markedly over time, it can be inferred that adsorption is interfering with the assay components. If the assay components are similar in nature to those being tested (e.g., where both the control and test elements are proteins) it can be inferred that adsorption is interfering with the test components as well.

Integration of Electroosmotic Suction Pumps

In one aspect, the present invention provides electroosmotic pump configurations which are used to deliver materials to selected regions during pressure or electroosmotic fluid flow, or combinations thereof. This pump can also be configured for reduced surface adsorption, e.g., by using AC in channels under control of the pump.

On chip electroosmotic flow can induce pressure driven flow using differential EP flow velocities in two connecting microchannels (patent application "Micropump" by Parce U.S. Ser. No. 08/937,958 filed Sep. 25, 1997). FIG. 1 illustrates one configuration for an on-chip suction pump. Such differential EO characteristics are achieved, e.g., by using buffers with different EO mobilities, use of preferential surface coatings to vary the zeta potentials, or packing microbeads with different zeta potential characteristics (see also, U.S. Ser. No. 60/127,825, "MANIPULATION OF MICROPARTICLES IN MICROFLUIDIC SYSTEMS" by Burd-Mehta et al.).

In these cases, the consistency of the EO pump depends on the characteristics of the buffer(s) used for pumping. In some assays, the buffer conditions favorable for, e.g., chemical reactions are not necessarily the properties desirable for EO pumping. In one aspect, this invention allows the separation of buffer requirements for chemical reactions and for EO pumping thus adding a much greater degree of flexibility in assay development.

Figure 2A:
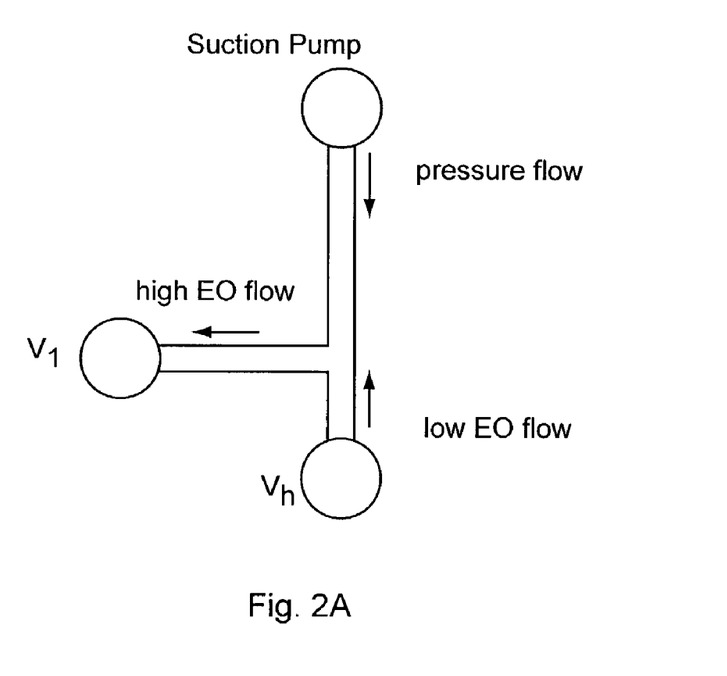
Figure 2B:
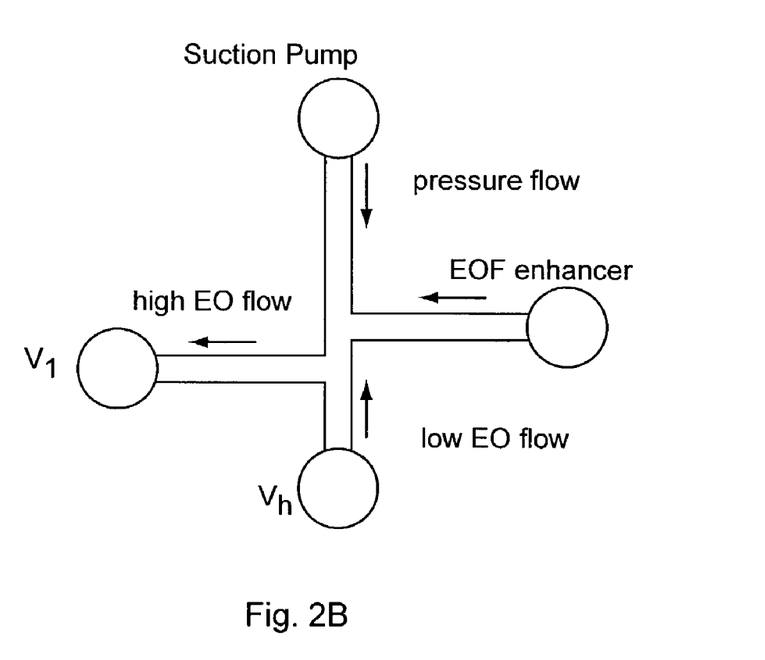

This invention provides the use of an additional channel connected near an EO pump junction to deliver a buffer with favorable EO pumping characteristics to enhance the efficiency of the pump. This idea is illustrated schematically in FIGS. 2A and 2B. The "EOF enhancer" buffer can be, e.g., a buffer with low ionic concentration, high pH, or can include a detergent to break up cells to prevent clogging of the "high EO flow" channel, or can have a high concentration of zwitterions to prevent protein sticking to the channel walls in the pump channels. The simplest way to deliver the enhancer buffer is by pressure driven flow generated by the on-chip pump. The geometries of the microchannel network determine the proportions of EO enhancer to assay buffer.

Other means of delivering the enhancer buffer, such as by additional on-chip pressure pumps, can also be used.

This improved EO pump is useful in general for generating pressure-based flow in microchannels. In addition, the improved EO pump can be used to drive flow in channels which comprise adsorption inhibition elements such as coupled AC power sources and adsorption inhibition agents.

Use of Adsorption Inhibitors

In testing a set of phosphatase enzyme assays conducted in a microscale apparatus using pressure-induced flow of the enzymes through microscale conduits, it was determined that 0.1M NDSB was not sufficient to inhibit adsorption of the enzyme to the walls of the conduits, as manifested by increasing background signal over time for the assays. Replacing NDSB with 0.1 mg/ml BSA was also insufficient to eliminated adsorption of the enzyme used in the assay. However, when both 0.1M NDSB and 0.1 mg/ml BSA were added, background signals were stable with time in a pressure-based flow pipettor device, showing that the combination of both compounds are effective in reducing adsorption. Higher concentrations of these adsorption inhibitor compounds are also effective, i.e., up to 1 M NDSB and 1 mg/ml BSA.

The discussion above is generally applicable to the aspects and embodiments of the invention described in the claims.

Moreover, modifications can be made to the method and apparatus described herein without departing from the spirit and scope of the invention as claimed, and the invention can be put to a number of different uses including the following:

The use of a microfluidic system comprising AC and pressure control elements.

The use of a microfluidic system as described herein, wherein a biochemical system flows through one of said channels substantially continuously, providing for, e.g., sequential testing of a plurality of test compounds.

The use of electrokinetic injection in a microfluidic device as described herein to modulate or achieve flow in the channels in conjunction with pressure-based flow mechanisms.

The use of a combination of wicks, electrokinetic injection and pressure based flow elements in a microfluidic device as described herein to modulate or achieve flow of materials e.g., in the channels of the device.

An assay utilizing a use of any one of the microfluidic systems or substrates described herein.

Microfluidic devices and bioassays which can be adapted to the present invention by the addition of concomitant electrical and pressure-induced flow include various PCT applications and issued U.S. patents, such as, U.S. Pat. No. 5,699,157 (J. Wallace Parce) issued Dec. 16, 1997, U.S. Pat. No. 5,779,868 (J. Wallace Parce et al.) issued Jul. 14, 1998, U.S. Pat. No. 5,800,690 (Calvin Y. H. Chow et al.) issued Sep. 1, 1998, and U.S. Pat. No. 5,842,787 (Anne R. Kopf-Sill et al.) issued Dec. 1, 1998; and published PCT applications, such as, WO 98/00231, WO 98/00705, WO 98/00707, WO 98/02728, WO 98/05424, WO 98/22811, WO 98/45481, WO 98/45929, WO 98/46438, and WO 98/49548, which are all incorporated herein by reference.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications and patent documents cited in this application are incorporated by reference in their entirety for all purposes to the same extent as if each individual publication or patent document were so individually denoted.

The invention claimed is:

1. A device or system comprising:
    a body having a plurality of fluidly coupled microchannels disposed therein;
    a source of fluidic material fluidly coupled to at least one of the plurality of microchannels;
    a fluid pressure controller fluidly coupled to the at least one microchannel;
    at least two electrodes in fluidic or ionic contact with the at least one microchannel; and
    an electrical controller in electrical contact with the at least two electrodes, the electrical controller configured to apply an electric field that produces movement of at least a portion of the fluidic material adjacent to a surface of the at least one microchannel while minimally influencing movement of the fluidic material in a direction of fluid flow or while minimally influencing movement of charged fluidic material in a direction of flow of the charged material.

2. The device or system of claim 1, wherein the electrical controller applies an alternating electrical field between the at least two electrodes.

3. The device or system of claim 1, wherein the electrical controller applies an electric field of sufficient duration and intensity to dislodge a protein from a surface of the at least one microchannel, or to prevent protein binding to a surface of the at least one microchannel.

4. The device or system of claim 1, wherein movement of the fluidic material in the at least one microchannel is directed primarily by pressure-based flow.

5. The device or system of claim 1, wherein movement of the fluidic material in the at least one microchannel is significantly directed by both pressure-based and electrokinetic flow.

6. The device or system of claim 1, wherein the body is fabricated from one or more material selected from: a ceramic, a glass, a polymer and a plastic material.

7. The device or system of claim 1, wherein the microchannel comprises at least one dimension between about 0.1 and 500 microns.

8. The device or system of claim 1, wherein the body comprises a plurality of intersecting microchannels.

9. The device or system of claim 1, wherein, during operation of the device, the fluid pressure controller and the electrical controller concomitantly apply a fluid pressure gradient and an electric field in the at least one channel.

10. The device or system of claim 1, the device further comprising a computer with an instruction set for simultaneously regulating electrical current and fluidic pressure in the at least one channel.

11. The device or system of claim 1, wherein, during operation of the device, a fluidic solution comprising an adherent material is flowed through the at least one channel under pressure controlled by the fluid pressure controller, wherein adherence of the adherent material to the at least one microchannel is modulated by application of an electrical field between the at least two electrodes.

12. The device or system of claim 11, the electrical controller comprising an alternating current electrical controller.

13. The device or system of claim 12, wherein the electrical controller generates a square wave field.

14. The device or system of claim 12, wherein the electrical controller generates a sine wave field.

15. The device or system of claim 11, the device further comprising a signal detector mounted proximal to a signal detection region, said detection region fluidly coupled to the at least one microchannel.

16. An integrated system for moving adherent materials in a microchannel, the integrated system comprising:
- a first microchannel fluidly coupled to a pressure source and to a plurality of electrodes;
- a fluid pressure modulator for applying or modulating pressure from the pressure source in the first microchannel;
- an electrical controller for applying or modulating current or voltage at least at two of the plurality of electrodes; and,
- a computer operably linked to the fluid pressure modulator, or to the fluid pressure source, and to the electrical controller, which computer comprises an instruction set for controlling the fluid pressure modulator and the electrical controller, which instruction set provides for reduced adsorption of the adherent materials to a surface of the microchannel during pressure-induced flow of the materials.

17. The integrated system of claim 16, wherein the electrical controller modulates current or voltage.

18. The integrated system of claim 16, wherein the pressure modulator modulates pressure in the first microchannel.

19. The integrated system of claim 16, further comprising a signal detector proximal to a signal detection zone which is fluidly coupled to the microchannel.

20. The integrated system of claim 16, the integrated system comprising a body structure having the first microchannel disposed therein.

21. The integrated system of claim 20, the body structure comprising a plurality of additional microchannels disposed therein, the plurality of additional microchannels being fluidly coupled to the first microchannel, at least one of the additional microchannels being fluidly coupled to a source of one or more fluidic reagents, the computer additionally comprising an instruction set which directs movement of at least one of the one or more fluidic reagents into the first microchannel.

22. The integrated system of claim 16, further comprising a source of a plurality of test compounds comprising a microwell plate and a pipettor channel coupled to the at least one microchannel, which pipettor channel draws test compounds from the microwell plate into the at least one microchannel by application of electrokinetic force or fluidic pressure, or both electrokinetic force and fluidic pressure.

23. The integrated system of claim 22, wherein the computer comprises an instruction set directing the electrical controller to apply an electric field in response to the rate of flow of the one or more fluidic component.

24. The integrated system of claim 16, further comprising a flow sensor, which sensor senses the rate of flow of one or more fluidic component in the microchannel.

* * * * *